(12) United States Patent
Cary et al.

(10) Patent No.: US 7,223,434 B2
(45) Date of Patent: May 29, 2007

(54) BLENDED BABY FOODS

(75) Inventors: Julie Cary, Asbury, NJ (US); Frances Alexandria Coletta, Fremont, MI (US); Douglas Neal Hocking, Hackettstown, NJ (US); Charles Mohs, Morristown, NJ (US)

(73) Assignee: Gerber Products Company, Fremont, MI (US)

( * ) Notice: Subject to any disclaimer, the term of this patent is extended or adjusted under 35 U.S.C. 154(b) by 137 days.

(21) Appl. No.: 10/295,283

(22) Filed: Nov. 15, 2002

(65) Prior Publication Data

US 2003/0157238 A1 Aug. 21, 2003

Related U.S. Application Data

(60) Provisional application No. 60/331,987, filed on Nov. 21, 2001, provisional application No. 60/339,836, filed on Dec. 10, 2001.

(51) Int. Cl.
*A23L 1/29* (2006.01)
*C11C 1/06* (2006.01)

(52) U.S. Cl. .......................... 426/601; 426/2; 426/656; 426/801

(58) Field of Classification Search .................... 426/2, 426/601, 656, 801, 21
See application file for complete search history.

(56) References Cited

U.S. PATENT DOCUMENTS

| | | | |
|---|---|---|---|
| 4,614,663 A | 9/1986 | Rule | |
| 5,444,054 A | 8/1995 | Garleb et al. | |
| 5,492,899 A | 2/1996 | Masor et al. | |
| 5,601,860 A | 2/1997 | Lien et al. | |
| 5,700,590 A | 12/1997 | Masor et al. | |
| 5,709,888 A | 1/1998 | Gil et al. | |
| 5,780,451 A | 7/1998 | DeMichele et al. | |
| 5,952,314 A | 9/1999 | DeMichele et al. | |
| 6,099,871 A | 8/2000 | Martinez | |
| 6,194,009 B1 | 2/2001 | Kamarel | |
| 6,596,766 B1* | 7/2003 | Igarashi et al. | 514/558 |
| 2003/0171433 A1* | 9/2003 | Kuchan et al. | 514/560 |
| 2004/0013787 A1 | 1/2004 | Theuer | |
| 2005/0042256 A1 | 2/2005 | Decombaz et al. | |
| 2005/0053713 A1 | 3/2005 | Birch et al. | |

FOREIGN PATENT DOCUMENTS

WO WO 2004/082402 9/2004

OTHER PUBLICATIONS

Hawley, G. The Condensed Chemical Dictionary, 10$^{th}$ Ed. Van Nostrand Reinhold Col. NY, 1981, p. 313.*
Cheon et al., "Effect of Dietary Linoleate/alpha-Linolenate Balance on the Brain Lipid Composition, Reproductive Outcome and Behavior of Rats during Their Prenatal and Postnatal Development", Biosci. Biotechnol. Biochem., vol. 64, No. 11, pp. 2290-2297, (2000).
Guidance Note on the implementation of European Communities (Infant Formulae and follow-on Formulae) Regulations, 1998 to 2000, Published by Food Safety Authority of Ireland, Dublin, pp. 39-45, (2001).
Scherz et al., "Food composition and nutrition tables, Human milk", Medpharm Scientific Publ., pp. 6-7, (2000).

* cited by examiner

*Primary Examiner*—Helen Pratt
(74) *Attorney, Agent, or Firm*—Radha Masilamani; John W. Kung; Diane E. Furman

(57) ABSTRACT

Processed baby foods are disclosed which are formulated with oils and/or nucleotides. Oils are added to yield an acceptable ratio of the essential fatty acids, linoleic acid (LA) and α-linolenic acid (ALA). A blend of 3–6 nucleotides may be added to yield a level of 3–6 mg/100 Kcal, which are associated with a number of biological processes, the most common being the potential to optimize the health of the immune and gastrointestinal systems of breast-fed infants and some infants and young children fed commercial infant formula with added nucleotides.

16 Claims, No Drawings

BLENDED BABY FOODS

This application claims the benefit of U.S. Provisional Application No. 60/331,987, filed Nov. 21, 2001, and U.S. Provisional Application No. 60/339,836, filed Dec. 10, 2001, both of which are hereby incorporated by reference in their entirety.

BACKGROUND OF THE INVENTION

This invention relates to processed baby foods to be consumed by human infants and young children from the age of about 6 months to 2 years (typically infants up to age 12 months) depending on the individual's particular stage of development and food needs. Baby foods, such as dry infant cereal, pureed foods and bakery items are well-known and have been commercially-formulated with additional key nutrients, e.g., iron, zinc, calcium, etc. In most cases, these foods are low in fat and must be carefully fed in the correct amounts to assure that infants consume an adequate amount of kilocalories (Kcals) to provide the energy required for healthy growth and development. When fat has been added by commercial processors to these foods, the ratio of two specific fatty acids (linoleic acid (LA) and α-linolenic acid (ALA)) has not been a consideration. Hence, infants who are transitioning from a high-fat liquid diet (breast milk or infant formula) to a lower-fat diet of processed baby foods (or homemade baby foods) may not be able to consume the full amount of energy and/or the correct ratios of these fatty acids, which are precursors for the synthesis of two critical long chain polyunsaturated fatty acids (LCPUFAs): arachidonic acid (AA) and docosahexaenoic acid (DHA). LCPUFAs are required for healthy infant growth, and support a broad range of metabolic processes necessary for development and/or functioning of the brain, retina and other nerve tissue.

Accordingly, there is a need for a fat blend designed for use in processed baby foods which addresses not only the quantity, but also the quality of fat with an acceptable LA:ALA ratio, thus increasing the likelihood that the energy and essential fatty acid requirements of rapidly growing infants are consistently met on a daily basis.

Similarly, breast milk and some infant formulas contain factors that have been identified as nucleotides useful to the optimized development of the immune and gastrointestinal systems. Nucleotides may be considered "conditionally essential" in rapidly growing infants living in adverse environments. The addition of these nucleotides may enhance health and growth.

Situations under which these components may become conditionally essential include certain disease states and periods of limited nutrient intake or rapid growth, along with the presence of various regulatory and developmental factors which interfere with the body's ability to synthesize nucleotides. Furthermore, when infants are transitioning to solid foods, exogenous sources of dietary nucleotides may be particularly important. Examples include: 1) the breast-fed infant whose intake of breast milk decreases to less than the recommended intake (600–720 mL) resulting in a concurrent decreased intake of nucleotides; and 2) the formula-fed infant whose diet is low in nucleotides. In addition, the first complementary foods are often cereal, fruits and vegetables, all of which are poor sources of nucleotides. Thus, nucleotides may be conditionally essential, with the prudent step being to provide the infant with an additional dietary source of these factors. There are no formulations for baby foods that are supplemented with nucleotides. Accordingly, there is a need for processed baby foods to be supplemented with these components for increasing the likelihood that the needs for nucleotides by rapidly growing infants, transitioning to complementary foods, are consistently met on a daily basis.

SUMMARY OF THE INVENTION

This invention concerns these three types of blends in processed baby foods:

A. Processed Baby Foods Comprising a Blend of Oils With an Acceptable LA:ALA Ratio A baby food comprising two fatty acids in an oil blend which delivers an acceptable ratio of essential fatty acids (i.e., an LA:ALA ratio by weight of 7–12:1), which is an ongoing requirement of infants transitioning from a high-fat diet of breast milk or infant formula to processed baby food. The composition for this blend is based on the ratio of oils used in infant formula that has been shown to not only be well-tolerated and absorbed, but which also supports growth and development in infants. Furthermore, this oil blend does not impart an objectionable taste or appearance to the food, is well-accepted by infants, and is easily incorporated into a wide range of processed baby foods. Also, the oil blend enhances the sensory properties of the baby food, as by masking the flavors of some fortificants, such as iron, zinc, etc., and provides a fuller mouthfeel and flavor.

B. Processed Baby Foods Comprising a Blend of 3–6 Nucleotides at an Acceptable Level per 100 Kcal A processed baby food comprising a blend of 3–6 nucleotides, to equal an acceptable level of 3–6 mg/100 Kcal, which may be conditionally essential for infants transitioning from a high-fat diet of breast milk or infant formula to processed baby foods who may not be consuming the recommended amount of 600–720 mL of breast milk or infant formula. Infant formula supplemented with nucleotides at this level has been shown to not only be well-tolerated and absorbed, but also to support growth and development in infants, age 3–8 months. This blend of nucleotides does not impart an objectionable taste or appearance, is well-accepted by infants, and is easily incorporated into a wide range of processed baby foods.

C. Processed Baby Foods Comprising Both a Blend of Oils With an Acceptable

LA:ALA Ratio and a Blend of 3–6 Nucleotides at an Acceptable Level per 100 Kcals As described in A and B above.

DETAILED DESCRIPTION

One aspect of the invention is a processed baby food comprising a 1.5–3.0% (preferably 2–2.5%; most preferably 2%) blend of oils comprising LA and ALA, in an LA:ALA ratio of 7–12:1 (preferably 8–10:1; more preferably 9–10:1; most preferably 9.35:1), all percentages wt/wt, wherein the oils are soy oil, high oleic sunflower oil, coconut oil or a combination of 2–3 of these oils. A combination of three oils is preferred.

Another aspect of the invention is a processed baby food comprising 3–6 nucleotides at a level of 3–6 mg/100 Kcal, selected from the group consisting of adenosine, cytidine, guanosine, uridine, inosine and thymidine. The level is preferably 4–5 mg/100 Kcal; most preferably 4.7 mg/100

Kcal. Preferably, five nucleotides are used, selected from the group consisting of adenosine, cytidine, guanosine, uridine and inosine.

Another aspect of the invention is a processed baby food comprising a 1.5–3.0% blend of oils comprising LA and ALA, in an LA:ALA ratio of 7–12:1, all percentages wt/wt., and 3–6 nucleotides at a level of 3–6 mg/100 Kcal, selected from the group consisting of adenosine, cytidine, guanosine, uridine, inosine and thymidine.

Yet another aspect of the invention is a method of supplementing the diet of an infant or young child of age 6–24 months with precursors for the synthesis of arachidonic acid and docosahexaenoic acid, which comprises feeding said infant a food comprising a blend of oils as described above.

A further aspect is a method of supplementing the diet of an infant or young child of age 6–24 months with nucleotides, which comprises feeding said child a food comprising 3–6 nucleotides as described above.

A further aspect is a method of supplementing the diet of an infant or young child of age 6–24 months with precursors for the synthesis of arachidonic acid and docosahexaenoic acid and with nucleotides, which comprises feeding said child a food comprising a blend of oils as described above and 3–6 nucleotides as described above.

The following terms are used herein.

"Infant" means a child from birth to 12 months of age.

"Young child" or "toddler" means a child from 13–36 months of age.

"Breast milk" means human milk.

Infant formulas are formulated, commercially processed, high-fat breast milk substitutes that can be a breast milk supplement or the sole source of nutrients, energy, and fluids required by infants for growth and development. Infant formulas are typically used up to about 6 months of age, then consumed in decreasing amounts through the age of 12 months, and beyond this age range for some young children.

The term "essential fatty acids" means the fatty acids that the body needs but cannot synthesize and must be supplied by the diet. The two main essential fatty acids are LA and ALA.

Nucleotides are compounds associated in a number of biological processes, the most common being the potential to optimize the health of the immune and gastrointestinal systems of breast-fed infants. Nucleotides consist of a base composed of nitrogen, 5-carbon sugars (ribose or deoxyribose), and one or three phosphate groups. The nitrogenous bases are primarily derived from amino acids that form either a purine or pyrimidine. The base (e.g., adenine) plus the sugar forms a nucleoside (e.g., adenosine) that is linked with a phosphate group to constitute the nucleotide (e.g., adenosine monophosphate (AMP)). The ribonucleotides and deoxyribonucleotides are the building blocks for the nucleic acids, RNA and DNA, respectively. The nucleotides used herein are adenosine (AMP), cytidine (CMP), guanosine (GMP), uridine (UMP), inosine (IMP) and thymidine (TMP). When all six nucleotides are included, amounts such as the following may be used:

| NUCLEOTIDE BLEND | | |
|---|---|---|
| Nucleotide | (mg/100 Kcal) | % in Blend |
| AMP | 0.54 | 1.08 | 18 |
| CMP | 1.14 | 2.28 | 38 |
| GMP | 0.30 | 0.60 | 10 |
| UMP | 0.63 | 1.26 | 21 |
| IMP | 0.09 | 0.18 | 3 |
| TMP | 0.30 | 0.60 | 10 |
| TOTAL | 3–6 | | 100 |

Energy refers to the kilocalories released by the metabolism of food, which must be supplied regularly to meet the fuel needs for a child's survival. Within this context, fat is defined as a concentrated source of energy that infants need to efficiently fuel their rapid growth demands (1 g of fat provides 9 Kcal/g vs. 4 Kcal/g of carbohydrate or protein.) During the first year of life, full-term infants typically double their birth weight by 4–5 months and triple it by 12 months of age. For premature and low birth weight infants, the rate of growth is even more rapid. Consequently, the driving force of infant food consumption is the need for energy to support growth and development.

Approximately 50% of the energy in breast milk and 40–50% in cow's milk-derived infant formula is provided by fat. Because babies have small stomach capacity, the calorically dense, easily digested fat in breast milk or infant formulas helps infants to effectively meet their energy demands.

During the commercial preparation of infant formulas, the butterfat of whole cow milk is replaced with a blend of vegetable oils or a mixture of vegetables oils and fats. This replacement improves fat digestibility and absorption, as well as provides the acceptable concentration and ratio of the essential fatty acids (LA and ALA in the recommended range of a minimum of 6:1 to a maximum of 16:1), which is referred to as the LA:ALA ratio. Additionally, some commercial infant formulas are supplemented with a blend of nucleotides at levels not to exceed the acceptable amount and composition present in upper limits of human milk, with the maximum specified range being 5.0–16.0 mg/100 Kcal.

At some point, infants and young children transition from a high-fat, nutritionally complete liquid diet of breast milk or infant formula (the nursing period) to either a complementary feeding period during which adult foods, liquids or processed baby foods are introduced to supplement breast milk or infant formula, or they go directly to a modified adult period where all of the nutrition comes from adult foods and liquids. The rate at which a child progresses through these stages is determined by its rate of growth, and by the maturation of the nervous system, intestinal tract and kidneys, which also impact the development of the physical and cognitive skills required for eating the various types of baby foods designed to match the a child's development during each of these stages.

Processed baby food refers to solids-containing foods that are to be given to or used by infants and young children from the age of about 6 months during the complementary feeding period or the modified adult period (typically up to 2 years of age but potentially even beyond this time frame), which is suitable either as a complement to breast milk or infant formula when either becomes insufficient to satisfy the nutritional requirements of the a child, or as a complete replacement for breast milk or infant formula. The foods may comprise any prepared fruit, vegetable, meat, cereal, dessert, bakery item, juice or combinations thereof in a wet or dry form suitable for a child's consumption. The size of any particulates in the processed baby foods depends on the level of developmental feeding skills of the infant to be fed, according to practices well-known in the art, and generally increase as the child grows. The minimum particle size is 7 mm; the solids content is at least 12% by weight. Juice means a liquid containing a solid nutrient extract or puree of one or more fruits or vegetables or combinations thereof. The term juice also includes a paste or concentrate of one or more fruits or vegetables or combinations thereof which has been reconstituted or intended to be reconstituted with a liquid, such as water, to obtain a final product of desired concentration, typically 12% by weight total solids. Thus, processed baby food includes, but is not limited to, ready-to-eat jarred foods, dried or instant foods, cereals, juices and bakery goods.

Serving sizes for processed baby foods are calculated in terms of "reference amounts", which are used as the standards herein. The reference amount is the quantity of food typically consumed by an infant or toddler per eating occasion. The various stages are used to distinguish baby foods designated for infants and toddlers of these different age ranges. Examples of reference amounts per product categories for infant and toddler foods are shown in Table 1.

The amounts of Kcals per serving for these various product categories vary widely, e.g., dried infant rice cereal, 60 Kcal/15 g; Stage 1 Carrots, 21 Kcal/60 g; Stage 2 Jarred Mixed Cereal with Applesauce & Bananas, 97 Kcal/110 g; Stage 2 Jarred Applesauce, 32 Kcal/60 g; Stage 2 Jarred Vegetable and Chicken Dinner, 37 Kcal/60 g; Stage 3 Jarred Vegetable Beef Dinner, 71 Kcal/110 g; Stage 3 Jarred Vanilla Custard Pudding, 103 Kcal/110 g; apple juice, 60 Kcal/1 20 mL; and ready-to-eat snacks for toddlers, 28 Kcal/7 g.

Similarly, the percent of Kcals from fat in various processed baby food products ranges from 28% in jarred dinners, with fruits and vegetables providing Kcals primarily from carbohydrates. Furthermore, the need for calorically dense baby foods increases as the percent of Kcals from complementary foods increases, with the range progressing from 40% (6–8 months); 54% at 9–11 months; and 69% (12–24 months). Hence, these lower fat baby foods must be carefully fed in the correct amounts to assure that infants and young children consume adequate Kcals and essential fatty acids.

A preferred aspect of the invention is a processed baby food for complementary feeding of infants which is formulated with 2% of an oil blend consisting of a combination of oils that has an LA:ALA ratio (wt/wt) of 9.35:1, as outlined in Table 2.

TABLE 1

Reference Amounts per Product Categories

| Examples of Product Category for Infant and Toddler Foods | Ref. Amount (g) | Stage and Age Range (months) | Product Attributes | Feeding Skills |
| --- | --- | --- | --- | --- |
| Dry instant cereal | 15 | STAGE 1 from about 6 | Single ingredient | Sits with help. Opens mouth as spoon approaches. |
| Prepared fruit, vegetable, strained type | 60 | STAGE 1 from about 6 | Single ingredient, smooth puree | Moves food to back of mouth and swallows without gagging. |
| Juice | 120 (mL) | STAGE 1 from about 6 | Single ingredients | |
| Prepared cereal | 110 | STAGE 2 from about 6–9 | >1 ingredient with thick puree | Sits alone. Learns to keep thick purees in mouth without gagging. |
| Prepared dinner, dessert, fruit, vegetable, or soup, strained types | 60 | STAGE 2 from about 6–9 | >1 ingredient with thick texture | Starts to drink from lidded cup with help. |
| Prepared dinner, dessert, fruit, vegetable, or soup, junior types | 110 | STAGE 3 from about 9–12 | >1 ingredient with complex flavors and particulates to formulate lumps | Crawls well and pulls self up to stand. Uses tongue to move food to side of mouth for mashing, grinding and chewing. |
| Ready-to-eat teething biscuits, cookies and toast | 7 for older infants | FINGER FOODS from about 9–24 | Texture to encourage chewing and finger-feeding | Holds small foods between thumb and first finger to self feed. |
| Prepared stew or soup for toddlers | 170 | TODDLER from about 12–24 | Foods with mature flavors and texture | Walks with assistance and stands alone. |
| Prepared vegetables for toddlers | 70 | TODDLER from about 12–24 | Continued chewing and self-feeding practice | Bites through a variety of textures. |
| Prepared fruits for toddlers | 125 | | | Feeds self with fingers; starts to use feeding utensils to feed self. |

TABLE 2

2% Oil Blend (LA and ALA)

| Oil Source | % LA | % ALA | Blend % | % LA Blend | % ALA Blend | Ratio in Total Blend of LA:ALA |
|---|---|---|---|---|---|---|
| Soy Oil | 53.7 | 7.6 | 25 | 13.425 | 1.9 | |
| High Oleic Sunflower Oil | 9.0 | 0 | 45 | 4.05 | 0 | |
| Coconut Oil | 1.9 | 0.1 | 30 | 0.57 | 0.03 | |
| Blend | | | 100 | 18.045 | 1.93 | 9.350 |

Nutrition from other foods will vary from child to child. In general, however, it is expected that the baby food of the invention will provide approximately 20–40% of the calories from fat. The blend of specific oils in examples of products for this invention is provided in Tables 3–6.

TABLE 3

Kcals From Fat and Per Serving (Formula without 2% Oil Blend)

| Product Example | Serving (g) | Serving (Kcal) | Kcal (per g) | Fat (g) | Kcals from Fat | % Kcals from Fat |
|---|---|---|---|---|---|---|
| 1st Stage Carrots | 60.0 | 21.0 | 0.4 | 0.0 | 0.0 | 0.0 |
| 2nd Stage Applesauce | 60.0 | 32.0 | 0.5 | 0.0 | 0.0 | 0.0 |
| 3rd Stage Vegetable Beef Dinner | 110.0 | 71.0 | 0.7 | 2.3 | 20.3 | 28.6 |
| Ready to Eat Bakery-Cereal Snacks | 7.0 | 28.0 | 4.0 | 0.7 | 6.3 | 22.5 |

TABLE 4

Kcals From Fat and Per Serving (Formula with 2% Oil Blend)

| Product Example | Oil Blend Replaces | Serving (g) | Oil Blend by wt. (g) | Added Kcals | Serving (Kcal) | Kcals (per g) | Fat (g) | Kcals from Fat | % Kcals from Fat |
|---|---|---|---|---|---|---|---|---|---|
| 1st Stage Carrots | Water | 60 | 1.2 | 10.8 | 31.8 | 0.5 | 1.2 | 10.8 | 34.0 |
| 2nd Stage Applesauce | Water | 60 | 1.2 | 10.8 | 42.8 | 0.7 | 1.2 | 10.8 | 25.2 |
| 3rd Stage Vegetable Beef Dinner | Other Fat | 110 | 2.2 | 0* | 71.0 | 0.7 | 2.3 | 20.3 | 28.6 |
| Ready to Eat Bakery-Cereal Snacks | Other Fat | 7 | 0.14 | 0* | 28.0 | 4.0 | 0.7 | 6.3 | 22.5 |

*The oil blend replaces existing fat sources in the formulation, therefore no change in Kcal/Serving is observed.

TABLE 5

Oil Blend Formulation at 2% by Weight

| Stage | Serving (g) | Serving (Kcal) | Oil Blend: g/Serving | | | Oil Blend: g/100 Kcal of Product* | | |
|---|---|---|---|---|---|---|---|---|
| | | | Soy Oil | Sunflower Oil | Coconut Oil | Soy Oil | Sunflower Oil | Coconut Oil |
| Stage 1 Carrots | 60 | 31.8 | 0.30 | 0.54 | 0.36 | 0.94 | 1.70 | 1.13 |
| Stage 2 Applesauce | 60 | 42.8 | 0.30 | 0.54 | 0.36 | 0.70 | 1.26 | 0.84 |
| Stage 3 Vegetable Beef Dinner | 110 | 71 | 0.55 | 0.99 | 0.66 | 0.77 | 1.39 | 0.93 |
| Ready-to-Eat Cereal Snacks | 7 | 28 | 0.04 | 0.06 | 0.04 | 0.13 | 0.23 | 0.15 |

TABLE 6

LA/ALA Contribution from 2% Oil Blend Addition or Substitution

| | | | La/ALA: g/serving | | | LA/ALA: g/100 Kcal* | | |
|---|---|---|---|---|---|---|---|---|
| Stage | Serving (g) | Serving (Kcal) | LA | ALA | LA:ALA | LA | ALA | LA:ALA |
| Stage 1 Carrots | 60 | 31.8 | 0.22 | 0.02 | 9.35 | 0.68 | 0.07 | 9.35 |
| Stage 2 Applesauce | 60 | 42.8 | 0.22 | 0.02 | 9.35 | 0.51 | 0.05 | 9.35 |
| Stage 3 Vegetable Beef Dinner | 110 | 71 | 0.40 | 0.04 | 9.35 | 0.56 | 0.06 | 9.35 |
| Ready-to-Eat Cereal Snacks | 7 | 28 | 0.03 | 0.00 | 9.35 | 0.09 | 0.01 | 9.35 |

Examples of the impact of formulating baby foods with the oil blend of Table 2 on the quality and quantity of Kcals from fat is summarized in Tables 7 and 8.

TABLE 7

Formula without Oil Blend

| Product Example | Serving (g) | Serving (Kcal) | Kcals from Fat | % Kcals from Fat |
|---|---|---|---|---|
| 1st Stage Carrots | 60.0 | 21.0 | 0.0 | 0.0 |
| 2nd Stage Applesauce | 60.0 | 32.0 | 0.0 | 0.0 |
| 3rd Stage Vegetable Beef Dinner | 110.0 | 71.0 | 20.3 | 28.6 |
| Ready to Eat Bakery-Cereal Snacks | 7.0 | 28.0 | 6.3 | 22.5 |

TABLE 8

Formula with 2% Oil Blend

| | | | | | Change In | |
|---|---|---|---|---|---|---|
| Product Example | Serving (g) | Serving (Kcal) | Kcals from Fat | % Kcals from Fat | Quantity | Quality |
| 1st Stage Carrots | 60 | 31.8 | 10.8 | 34.0 | X | X |
| 2nd Stage Applesauce | 60 | 42.8 | 10.8 | 25.2 | X | X |
| 3rd Stage Vegetable Beef Dinner* | 110 | 71.0 | 20.3 | 28.6 | | X |
| Ready-to-Eat Bakery-Cereal Snacks* | 7 | 28.0 | 6.3 | 22.5 | | X |

*The oil blend replaces existing fat sources in the formulation, therefore no change in Kcal/Serving is observed.

Another aspect of the invention is a processed baby food for complementary feeding, formulated with 3–6 nucleotides to equal a level of 3–6 mg/100 Kcal. Formulations for a blend of nucleotides, in examples of products per serving and 100 Kcals for this invention, are outlined in Tables 9 and 10.

TABLE 9

Formulations With Nucleotide Blend

| | | | mg/Serving | | | | | |
|---|---|---|---|---|---|---|---|---|
| Product Example | Serving (g) | Serving (Kcal) | AMP | GMP | IMP | CMP | UMP | TOTAL |
| Stage 1 Carrots | 60 | 21 | 0.180 | 0.090 | 0.030 | 0.479 | 0.210 | 0.988 |
| Stage 2 Applesauce | 60 | 32 | 0.274 | 0.137 | 0.046 | 0.729 | 0.319 | 1.505 |

TABLE 9-continued

Formulations With Nucleotide Blend

| Product Example | Serving (g) | Serving (Kcal) | AMP | GMP | IMP | CMP | UMP | TOTAL |
|---|---|---|---|---|---|---|---|---|
| Stage 3 Vegetable Beef Dinner | 110 | 71 | 0.608 | 0.304 | 0.102 | 1.617 | 0.708 | 3.339 |
| Ready-to-Eat Cereal Snacks | 7 | 28 | 0.240 | 0.120 | 0.040 | 0.638 | 0.279 | 1.317 |

| | mg/100 Kcal | | | | | |
|---|---|---|---|---|---|---|
| Product Example | AMP | GMP | IMP | CMP | UMP | TOTAL |
| Stage 1 Carrots | 0.855 | 0.428 | 0.143 | 2.280 | 0.998 | 4.704 |
| Stage 2 Applesauce | 0.855 | 0.428 | 0.143 | 2.280 | 0.998 | 4.704 |
| Stage 3 Vegetable Beef Dinner | 0.855 | 0.428 | 0.143 | 2.280 | 0.998 | 4.704 |
| Ready-to-Eat Cereal Snacks | 0.855 | 0.428 | 0.143 | 2.280 | 0.998 | 4.704 |

TABLE 10

Formulations With 2% Oil Blend and Nucleotide Blend

| Product Example | Serving (g) | Serving (Kcal) | AMP | GMP | IMP | CMP | UMP | TOTAL |
|---|---|---|---|---|---|---|---|---|
| Stage 1 Carrots | 60 | 31.8 | 0.272 | 0.136 | 0.045 | 0.725 | 0.317 | 1.496 |
| Stage 2 Applesauce | 60 | 42.8 | 0.366 | 0.183 | 0.061 | 0.976 | 0.427 | 2.014 |
| Stage 3 Vegetable Beef Dinner | 110 | 71 | 0.608 | 0.304 | 0.102 | 1.617 | 0.708 | 3.339 |
| Ready-to-Eat Cereal Snacks | 7 | 28 | 0.240 | 0.120 | 0.040 | 0.638 | 0.279 | 1.317 |

| | mg/100 Kcal | | | | | |
|---|---|---|---|---|---|---|
| Product Example | AMP | GMP | IMP | CMP | UMP | TOTAL |
| Stage 1 Carrots | 0.855 | 0.428 | 0.143 | 2.280 | 0.998 | 4.704 |
| Stage 2 Applesauce | 0.855 | 0.428 | 0.143 | 2.280 | 0.998 | 4.704 |
| Stage 3 Vegetable Beef Dinner | 0.855 | 0.428 | 0.143 | 2.280 | 0.998 | 4.704 |
| Ready-to-Eat Cereal Snacks | 0.855 | 0.428 | 0.143 | 2.280 | 0.998 | 4.704 |

The invention is further defined by reference to the following examples, which are intended to be illustrative and not limiting. The Oil Blend used in the Examples is as shown in Table 2. The following blend (hereinafter, Nucleotide Blend) is used in the examples:

NUCLEOTIDE BLEND

| Nucleotide | mg/100 Kcal | % in Blend |
|---|---|---|
| AMP | 0.855 | 18.176 |
| CMP | 2.280 | 48.469 |
| GMP | 0.428 | 9.099 |
| UMP | 0.998 | 21.258 |
| IMP | 0.143 | 3.040 |
| Total Blend | 4.704 | 100.000 |

EXAMPLE 1

Stage 1 Carrots Formulated With Oil Blend

A 1000 kg batch is formulated, comprised of pureed carrots, water, and 20 kg of the Oil Blend, which is then adjusted to a targeted viscosity. Next, the batch is thoroughly mixed to properly distribute the raw materials and heated to the required filling temperature. The product is packaged into containers and hermetically sealed. Next, the sealed containers are processed using commercially-accepted thermal processing techniques. The packages are commercially sterile.

EXAMPLE 2

Stage 2 Applesauce Formulated With Oil Blend

A 1000 kg batch is formulated, comprised of pureed fruit, sugar, modified starch, Vitamin C, water and 20 kg of the Oil Blend, which is then adjusted to a targeted viscosity. Next, the batch is mixed thoroughly to properly distribute the raw materials and heated to the required filling temperature. The product is packaged into containers and hermetically sealed. The sealed containers are then processed, using commercially-accepted thermal processing techniques. The packages are commercially sterile.

EXAMPLE 3

Stage 3 Vegetables and Beef Dinner Formulated With Oil Blend

A 1000 kg batch is formulated, comprised of beef, vegetables, grains, water and 20 kg of the Oil Blend, which is then adjusted to a targeted viscosity. Next, the batch is thoroughly mixed to properly distribute the raw materials and heated to the required filling temperature. The product is packaged into containers and hermetically sealed. The sealed containers are then processed, using commercially-accepted thermal processing techniques. The packages are commercially sterile.

EXAMPLE 4

Ready-to-Eat Cereal Snacks Formulated With Oil Blend

A 1000 kg batch is formulated, comprised of flour, vitamins, minerals, sugar, water, flavoring and 20 kg of the Oil Blend, which are mixed together. Next, the dough is blended, baked and cut to size, then packaged.

EXAMPLE 5

Stage 1 Carrots with Formulated With Nucleotide Blend

A 1000 kg batch is formulated, comprised of pureed carrots, water and 16.47 g of the Nucleotide Blend, which is adjusted to a targeted viscosity. Based on a 60 g serving of 21 Kcal, the nucleotide addition equals 4.704 mg/100 Kcal or 1.647 mg/100 g of product. Next, the batch is thoroughly mixed to properly distribute the raw materials and heated to the required filling temperature. The product is packaged into containers and hermetically sealed. The sealed containers are then processed, using commercially-accepted thermal processing techniques. The packages are commercially sterile.

EXAMPLE 6

Stage 2 Applesauce Formulated With Nucleotide Blend

A 1000 kg batch is formulated, comprised of pureed fruit, sugar, modified starch, Vitamin C, water and 25.09 g of the Nucleotide Blend, which is adjusted to a targeted viscosity. Based on a 60 g serving of 32 Kcal, the nucleotide addition equals 4.704 mg/100 Kcal or 2.509 mg/100 g of product. Next, the batch is mixed thoroughly to properly distribute the raw materials, and heated to the required filling temperature. The product is packaged into containers and hermetically sealed. The sealed containers are then processed, using commercially-accepted thermal processing techniques. The packages are commercially sterile.

EXAMPLE 7

Stage 3 Vegetables and Beef Dinner Formulated With Nucleotide Blend

A 1000 kg batch is formulated, comprised of beef, vegetables, grains, water and 30.36 g of the Nucleotide Blend, which is then adjusted to a targeted viscosity. Based on a 110 g serving of 71 Kcal, the nucleotide addition equals 4.704 mg/100 Kcal or 3.036 mg/100 g of product. Next, the batch is thoroughly mixed to properly distribute the raw materials and heated to the required filling temperature. The product is packaged into containers and hermetically sealed. The sealed containers are then processed, using commercially-accepted thermal processing techniques. The packages are commercially sterile.

EXAMPLE 8

Ready-to-Eat Cereal Snacks Formulated With Nucleotide Blend

A 1000 kg batch is formulated, comprised of flour, vitamins, minerals, sugar, water, flavoring and 188.0 g of the Nucleotide Blend, which are then mixed together. Based on a 7 g serving of 28 Kcal, the nucleotide addition equals 4.704 mg/100 Kcal or 18.80 mg/100 g of product. Next, the dough is blended, baked, cut to size and packaged.

EXAMPLE 9

Stage 1 Carrots Formulated With Oil Blend and Nucleotide Blend

A 1000 kg batch is formulated, comprised of pureed carrots, water, 20 kg of the Oil Blend and 24.93 g of the Nucleotide Blend, which is then adjusted to a targeted viscosity. Based on a 60 g serving of 31.8 Kcal, the nucleotide addition equals 4.704 mg/100 Kcal or 2.493 mg/100 g of product. Next, the batch is thoroughly mixed to properly distribute the raw materials, and heated to the required filling temperature. The product is packaged into containers and hermetically sealed. The sealed containers are then processed, using commercially-accepted thermal processing techniques. The packages are commercially sterile.

EXAMPLE 10

Stage 2 Applesauce Formulated With Oil Blend and Nucleotide Blend

A 1000 kg batch is formulated, comprised of pureed fruit, sugar, modified starch, Vitamin C, water, 20 kg of the Oil Blend and 33.56 g of the Nucleotide Blend, which is then adjusted to a prescribed viscosity. Based on a 60 g serving of 42.8 Kcal, the nucleotide addition equals 4.704 mg/100 Kcal or 3.356 mg/100 g of product. Next, the batch is mixed thoroughly to properly distribute the raw materials, and is heated to the required filling temperature. The product is packaged into containers and hermetically sealed. The sealed containers are then processed, using commercially-accepted thermal processing techniques. The packages are commercially sterile.

EXAMPLE 11

Stage 3 Vegetables and Beef Dinner Formulated With Oil Blend and Nucleotide Blend A 1000 kg batch is formulated, comprised of beef, vegetables, grains, water, 20 kg of the Oil Blend and 30.36 g of the Nucleotide Blend, which is then adjusted to a targeted viscosity. Based on a 110 g serving of 71 Kcal, the nucleotide addition equals 4.704 mg/100 Kcal or 3.036 mg/100 g of product. Next, the batch is thoroughly mixed to properly distribute the raw materials, and heated to the required filling temperature. The product is packaged into containers and hermetically sealed. The sealed containers are then processed, using commercially-accepted thermal processing techniques. The packages are commercially sterile.

EXAMPLE 12

Ready-to-Eat Cereal Snacks Formulated With Oil Blend and Nucleotide Blend

A 1000 kg batch is formulated, comprised of flour, vitamins, minerals, sugar, water, flavoring, 20 kg of the Oil Blend and 188.0 g of the Nucleotide Blend, which are mixed together. Based on a 60 g serving of 21 Kcal, the nucleotide addition equals 4.704 mg/100 Kcal or 18.80 mg/100 g of product. The dough is blended and baked, then cut to size and packaged.

What is claimed is:

1. A processed baby food comprising a 1.5–3.0% blend of oils comprising linoleic acid, LA, and α-linolenic acid, ALA, in an LA:ALA ratio of 7–12:1, all percentages wt/wt, wherein the processed baby food is not an infant formula.

2. A baby food of claim 1, wherein the ratio is 8–10:1.

3. A baby food of claim 1, wherein the ratio is 9–10:1.

4. A baby food of claim 1, wherein the ratio is 9.35:1.

5. A baby food of claim 1, wherein the oils are soy oil, high oleic sunflower oil, coconut oil, or a combination of 2–3 of these oils.

6. A method of supplementing the diet of a child about 6–24 months of age with precursors for the synthesis of arachidonic acid (AA) and docosahexaenoic acid (DHA), which comprises feeding said child a food of claim 1.

7. The processed baby food of claim 1, wherein the processed baby food is at least one of a fruit, a vegetable, a meat, a cereal, a dessert, a bakery item and/or, a juice.

8. A processed baby food comprising a 1.5–3.0% blend of oils comprising LA and ALA, in an LA:ALA ratio of 7–12:1, all percentages wt/wt., and 3–6 nucleotides at a level of 3–6 mg/100 Kcal, selected from the group consisting of adenosine, cytidine, guanosine, uridine, inosine and thymidine, wherein the processed baby food is not an infant formula.

9. A method of supplementing the diet of a child about 6–24 months of age with nucleotides, which comprises feeding said child a food of claim 8.

10. A method of supplementing the diet of a child of about 6–24 months of age with precursors for the synthesis of AA and DHA and with nucleotides, which comprises feeding said child a food of claim 8.

11. The processed baby food of claim 8, wherein the processed baby food is at least one of a fruit, a vegetable, a meat, a cereal, a dessert, a bakery item and/or, a juice.

12. The processed baby food of claim 8, wherein the processed baby food is at least one of a fruit, a vegetable, a meat, a cereal, a dessert, a bakery item and/or, a juice.

13. The processed baby food of claim 8, wherein the following nucleotides are present in the following amounts: adenosine in an amount from 0.54 to 1.08 mg/100 Kcal, cytidine in an amount from 1.14 to 2.28 mg/100 Kcal, guanosine in an amount from 0.30 to 0.60 mg/100 Kcal, uridine in an amount from 0.63 to 1.26 mg/100 Kcal, inosine in an amount from 0.09 to 0.18 mg/100 Kcal, and thymidine in an amount from 0.30 to 0.60 mg/100 Kcal.

14. The processed baby food of claim 8, wherein the nucleotides are present at a level of 4–5 mg/100 Kcal.

15. The processed baby food of claim 8, wherein thymidine is present in the processed baby food.

16. The processed baby food of claim 8, wherein the following nucleotides are present in the following amounts: adenosine in an amount from 0.54 to 1.08 mg/100 Kcal, cytidine in an amount from 1.14 to 2.28 mg/100 Kcal, guanosine in an amount from 0.30 to 0.60 mg/100 Kcal, uridine in an amount from 0.63 to 1.26 mg/100 Kcal, inosine in an amount from 0.09 to 0.18 mg/100 Kcal, and thymidine in an amount from 0.30 to 0.60 mg/100 Kcal.

* * * * *